(12) United States Patent
Goldkuhl et al.

(10) Patent No.: US 8,948,838 B2
(45) Date of Patent: Feb. 3, 2015

(54) SWITCH PROBE FOR MULTIPLE ELECTRODE MEASUREMENT OF IMPEDANCE

(75) Inventors: Fredrik Goldkuhl, Sundyberg (SE); Marcus Gunnarsson, Uppsala (SE); Ulrik Birgersson, Stockholm (SE)

(73) Assignee: Scibase AB, Stockholm (SE)

( * ) Notice: Subject to any disclaimer, the term of this patent is extended or adjusted under 35 U.S.C. 154(b) by 260 days.

(21) Appl. No.: 13/146,245

(22) PCT Filed: Jan. 27, 2009

(86) PCT No.: PCT/EP2009/000509
§ 371 (c)(1),
(2), (4) Date: Jul. 26, 2011

(87) PCT Pub. No.: WO2010/085969
PCT Pub. Date: Aug. 5, 2010

(65) Prior Publication Data
US 2011/0282180 A1 Nov. 17, 2011

(51) Int. Cl.
*A61B 5/053* (2006.01)
*A61B 5/00* (2006.01)

(52) U.S. Cl.
CPC .............. *A61B 5/0531* (2013.01); *A61B 5/444* (2013.01); *A61B 5/685* (2013.01); *A61B 2562/0209* (2013.01); *A61B 2562/043* (2013.01)
USPC ............................. 600/382; 600/393; 600/547

(58) Field of Classification Search
CPC ...... A61B 5/1109; A61B 5/445; A61B 5/053; A61B 5/0531; A61B 5/0536
USPC ................... 600/372, 382, 393, 547; 128/898
See application file for complete search history.

(56) References Cited

U.S. PATENT DOCUMENTS 4,078,553 A 3/1978 Duroux
5,353,802 A * 10/1994 Ollmar .......................... 600/547
(Continued)

FOREIGN PATENT DOCUMENTS

EP 1437091 A1 7/2004
EP 1600104 A1 11/2005
(Continued)

OTHER PUBLICATIONS

Åberg, "Skin Cancer as Seen by Electrical Impedance," Medical Engineering, Department of Laboratory Medicine, Karolinska Institute, Stockholm, Sweden, 2004, 105 pages.
(Continued)

*Primary Examiner* — Lee S Cohen
*Assistant Examiner* — Erin M Cardinal
(74) *Attorney, Agent, or Firm* — Birch, Stewart, Kolasch & Birch, LLP

(57) ABSTRACT

The present invention provides impedance data having an improved spatial resolution, both with regard to depth and lateral extension, which enables a detection of diseased skin conditions, such a malignant melanoma, at an early stage. Specifically, the present invention is implemented in a probe, medical devices and medical systems including such a probe, and methods using such a probe for measuring electrical impedance of tissue of a subject. A switching circuit is arranged for selectively activate electrode pairs of the probe in accordance with a predetermined activation scheme, the predetermined activation scheme including to activate adjacent electrodes in a successive manner, to gradually scan tissue of the subject at a first tissue depth so as to obtain a sequence of impedance signals from the tissue depth.

15 Claims, 2 Drawing Sheets

(56) References Cited

U.S. PATENT DOCUMENTS

| | | | |
|---|---|---|---|
| 5,807,251 A * | 9/1998 | Wang et al. | 600/407 |
| 5,987,346 A | 11/1999 | Benaron et al. | |
| 6,845,264 B1 * | 1/2005 | Skladnev et al. | 600/547 |
| 6,962,587 B2 | 11/2005 | Johnson et al. | |
| 2002/0038101 A1 * | 3/2002 | Avrahami et al. | 604/20 |
| 2002/0045838 A1 * | 4/2002 | Treppo et al. | 600/547 |
| 2003/0078482 A1 | 4/2003 | Kenan et al. | |
| 2003/0176808 A1 * | 9/2003 | Masuo | 600/547 |
| 2004/0127780 A1 * | 7/2004 | Ollmar et al. | 600/365 |
| 2004/0242989 A1 * | 12/2004 | Zhu et al. | 600/407 |
| 2006/0085048 A1 * | 4/2006 | Cory et al. | 607/48 |
| 2006/0270942 A1 * | 11/2006 | McAdams | 600/547 |
| 2008/0057526 A1 * | 3/2008 | Caduff et al. | 435/14 |
| 2008/0221474 A1 * | 9/2008 | Waffenschmidt et al. | 600/547 |
| 2009/0326407 A1 * | 12/2009 | Tournefier et al. | 600/547 |
| 2010/0191141 A1 * | 7/2010 | Aberg | 600/547 |
| 2010/0298680 A1 * | 11/2010 | Talary et al. | 600/347 |
| 2011/0046505 A1 * | 2/2011 | Cornish et al. | 600/547 |
| 2011/0224520 A1 * | 9/2011 | Skerl et al. | 600/345 |
| 2013/0046165 A1 * | 2/2013 | Cassidy et al. | 600/386 |

FOREIGN PATENT DOCUMENTS

| | | |
|---|---|---|
| JP | 9-510014 A | 10/1997 |
| JP | 2007-502675 A | 2/2007 |
| WO | WO 92/06634 A1 | 4/1992 |
| WO | WO 95/24155 A1 | 9/1995 |
| WO | WO 96/12439 A1 | 5/1996 |
| WO | WO 01/43630 A2 | 6/2001 |
| WO | WO 01/52731 A1 | 7/2001 |
| WO | WO 01/64095 A2 | 9/2001 |
| WO | WO 2004/049937 A1 | 6/2004 |
| WO | WO 2005/018432 A2 | 3/2005 |
| WO | WO 2005/018432 A3 | 3/2005 |
| WO | WO 2005120332 A1 * | 12/2005 |
| WO | WO 2007/068433 A2 | 6/2007 |
| WO | WO 2009/018620 A1 | 2/2009 |
| WO | WO 2010/086326 A2 | 8/2010 |

OTHER PUBLICATIONS

Kapoor, "Bioelectric Impedance Techniques for Clinical Detection of Skin Cancer," A Thesis, University of Missouri-Rolla, 2001, 101 pages.

Aberg, P., "Assessment of skin lesions and skin cancer using simple electrical impedance indices.", Skin Res Technol, Aug. 2003, vol. 9, No. 3: pp. 257-61. Abstract Only.

Jie et al., "Comparison of Linear and Non-linear PCA, ICA in Feature Extraction", Conference on Academic Exchange of Postgraduates of Beijing Universities 2006—Communication and Information Technology Conference Proceedings (part II), 2006, pp. 1019-1023.

Beetner et al., "Differentiation Among Basal Cell Carcinoma, Benign Lesions, and Normal Skin Using Electric Impedance," IEEE Transactions on Biomedical Engineering, vol. 50, No. 8, Aug. 2003, pp. 1020-1025, XP011098743.

Emtestam et al., "Electrical Impedance of Nodular Basal Cell Carcinoma: A Pilot Study," Clinical and Laboratory Investigations, Dermatology, vol. 197, 1998, pp. 313-316, XP008026174.

Har-Shai et al. "Electrical Impedance Scanning for Melanoma Diagnosis: A Validation Study," Diagnosis of Melanoma, Plastic and Reconstructive Surgery, vol. 116, No. 3, Sep. 1, 2005, pp. 782-790, XP009123821.

Ravindran et al., "Impedance Scanner," Annual International Conference of the IEEE Engineering in Medicine and Biology Society, RCE Dept. College of Engineering, Guindy, Madras-25, India, vol. 12, No. 1, 1990, pp. 0120-0121, XP010035967.

* cited by examiner

SWITCH PROBE FOR MULTIPLE ELECTRODE MEASUREMENT OF IMPEDANCE

TECHNICAL FIELD

The present invention generally relates to the field of diagnosis of biological conditions and to a probe, medical apparatus and methods for non-invasively measuring impedance of tissue of living subjects and for using the measured impedance in the diagnosis of biological conditions of the tissue, for example, the presence of skin cancer, e.g. malignant melanoma or basal cell carcinoma. In particular, the present invention provides impedance data having an improved spatial resolution, both with regard to depth and lateral extension, which enables a detection of diseased skin conditions, such a malignant melanoma, at an early stage.

BACKGROUND ART

Electrical impedance is a very sensitive indicator of minute changes in organic and biological material and especially tissues such as mucous membranes, skin and integuments of organs, including changes due to irritation of caused by different reactions. Therefore, a lot of efforts have been made to find a convenient way to measure variations and alterations in different kinds of organic and biological material to be able to establish the occurrence of such alterations which are due to different states, characteristics or irritations from e.g. diseases. Such disease includes Squamos cell carcinoma (SCC), malignant melanoma, and basal cell carcinoma (BCC), which is the most common skin cancer. Its incidence is increasing in many countries throughout the world. Exposure to ultraviolet light or ionizing radiation increases the risk for developing BCC and other tumours as well as long term immunosuppression in connection with, for example, an allogeneic organ transplantation. There seems to be no apparent genetic connection and in many patients no other predisposing factors have been found. Traditionally, skin tumours, such as malignant melanoma, have been diagnosed by means of ocular inspection by the dermatologist, in combination with skin biopsy. However, clinical diagnosis of skin tumours is proven to be difficult even for experienced dermatologists, especially in the case of pigmented lesions. In the clinic there is thus a need for a diagnostic aid besides the established method of ocular inspection by the dermatologist in combination with skin biopsies for histological examination.

In light of this, significant work has been done in order to develop diagnostic tools for the diagnosis of tumours in the skin based on impedance measurements. In WO 92/06634 a device for non-invasive measurement of electrical impedance of organic and biological material is presented. The device includes a probe having a number of concentric ring electrodes. The electrodes are driven from a control unit in such a way that the electrical current path defining the actual tissue under test is pressed towards the surface of the tissue part under test. By varying a control signal it is possible to select the region to be tested. The capability of a control electrode to vary depth penetration is limited by the shapes, sizes and distances of the electrodes and the dominating factor determining the depth penetration is distance between the electrodes.

WO 01/52731 discloses a medical electrode for sensing electric bio-potentials created within the body of a living subject. The electrode comprises a number of micro-needles adapted to penetrate the skin. The micro-needles are long enough to reach the stratum cornium and penetrate at least into the stratum corneum and are electrically conductive on their surface and connected to each other to form an array. In EP 1 437 091, an apparatus for diagnosis of biological conditions using impedance measurements of organic and biological material is disclosed. The apparatus comprises a probe including a plurality of electrodes, where each electrode is provided with a number of micro-needles each having a length being sufficient to penetrate at least into stratum corneum. The micro-needles according to EP 1 437 091 are also "nail-like", i.e. they have stem having a substantially circular cross-section with a constant or a gradually decreasing diameter and a tip-portion with a substantially spherical or needle-shaped tip.

However, clinical experience has shown that lesions, especially in early stages, include very small malignant parts, sometimes being of the magnitude down to 1 mm or less. It has further been shown that it is very difficult or almost impossible to identify such small malignant parts of diseased tissues using the prior art methods and devices due to the limited or coarse spatial resolution, both with regard to tissue depth and with regard to a lateral dimension of the tissue (i.e. in tissue layer being parallel with the surface of the skin), in the impedance spectra obtained by means of these prior art methods. It is important to detect the diseased condition, e.g. malignant melanoma, at an early stage, since the prognosis for the patient will be improved significantly since proper treatment can be initiated when the malignant part still is small. Hence, there is an evident risk using the prior art methods that diseased skin conditions such as malignant melanoma at early stage conditions are not observed due to this limited or coarse spatial resolution.

In light of this, there is a need within the art of a device and method that provides an improved spatial resolution, both in a depth dimension and in a lateral dimension, of the obtained impedance spectra in order to enable detection of diseased conditions such as malignant melanoma at an early stage.

SUMMARY OF THE INVENTION

An object of the present invention is to present an improved probe, device and method for measuring human skin impedance with a high degree of accuracy and reliability.

Another object of the present invention is to provide an improved probe, device and method for measuring human skin impedance with an improved spatial resolution, both in a depth dimension and in a lateral dimension.

A further object of the present invention is to provide an improved probe, device and method for spatial scanning a selected tissue layer, both in a depth dimension and in a lateral dimension.

These and other objects of the present invention are achieved by a device and method as claimed in the independent claims. Further embodiments are defined in the dependent claims.

The term "depth dimension" refers to a dimension that extends in a direction from the outmost skin layer and into the tissue. Further, the term "lateral dimension" refers to a dimension that extends in a direction substantially parallel with the outmost skin layer, but at different tissue layers in the depth dimension. Thus, the term "spatial resolution" refers to a resolution in the depth dimension as well as in the lateral dimension.

According to a first aspect of the present invention, there is provided a probe for measuring electrical impedance of tissue of a subject comprising a plurality of electrodes, the electrodes being adapted to be placed in direct contact with the skin of the subject, and being connectable to an impedance measuring circuit adapted to apply a voltage and to measure a resulting current to determine an impedance signal. The probe further comprises a switching circuit for selectively activate electrode pairs by connecting at least two of electrodes with the impedance measuring circuit and disconnecting the remaining electrodes from the impedance circuit, wherein the voltage is applied at the two electrodes and the resulting current is measured between the at least two electrodes. The switching circuit is adapted to receive control signals instructing the switching circuit to activate electrode pairs in accordance with a predetermined activation scheme, the predetermined activation scheme including to activate adjacent electrodes in a successive manner to gradually scan tissue of the subject at a first tissue depth so as to obtain a sequence of impedance signals from the tissue depth.

According to a second aspect of the present invention, there is provided a measurement device for measuring electrical impedance of tissue of a subject comprising a probe having a plurality of electrodes, the electrodes being adapted to be placed in direct contact with the skin of the subject, and an impedance measuring circuit adapted to apply a voltage at two of the electrodes and to measure a resulting current to determine an impedance signal. The measurement device further comprises a switching circuit for selectively activate electrode pairs by connecting at least two of electrodes with the impedance measuring circuit and disconnecting the remaining electrodes from the impedance circuit, wherein the voltage is applied at the two electrodes and the resulting current is measured between the at least two electrodes; and a control device adapted to control the switching circuit to activate electrodes in accordance with a predetermined activation scheme, the predetermined activation scheme including to activate adjacent electrodes in a successive manner to gradually scan tissue of the subject at a first tissue depth so as to obtain a sequence of impedance signals from the tissue depth.

According to a third aspect of the present invention, there is provided a medical system for diagnosing a diseased condition of the skin of a subject comprising a probe for measuring electrical impedance of tissue of a subject, which probe is provided with a plurality of electrodes adapted to be placed in direct contact with the skin of the subject. The system further comprises an impedance measuring circuit adapted to apply a voltage at two of the electrodes and to measure a resulting current to determine an impedance signal; a switching circuit for selectively activate electrode pairs by connecting at least two of electrodes with the impedance measuring circuit and disconnecting the remaining electrodes from the impedance circuit, wherein the voltage is applied at the two electrodes and the resulting current is measured between the at least two electrodes; a control device adapted to control the switching circuit to activate electrodes in accordance with a predetermined activation scheme, the predetermined activation scheme including to activate adjacent electrodes in a successive manner to gradually scan tissue of the subject at a first tissue depth so as to obtain a sequence of impedance signals from the tissue depth; and a diagnosing unit being adapted to obtain the sequence of impedance signals and to deliver a diagnosis of a diseased condition of the tissue based on the measured impedance signals and reference values.

According to a fourth aspect of the present invention, there is provided a method for diagnosing a diseased condition of the skin of a subject utilizing a probe for measuring electrical impedance of tissue of a subject. The probe is provided with a plurality of electrodes adapted to be placed in direct contact with the skin of the subject. The method includes applying a voltage at two of the electrodes, measuring a resulting current to determine an impedance signal, selectively activating electrode pairs by connecting at least two of electrodes with the impedance measuring circuit and disconnecting the remaining electrodes from the impedance circuit, wherein the voltage is applied at the two electrodes and the resulting current is measured between the at least two electrodes, gradually scanning tissue of the subject at a first tissue depth so as to obtain a sequence of impedance signals from the tissue depth by controlling activation of electrodes in accordance with a predetermined activation scheme, the predetermined activation scheme including activating adjacent electrodes in a successive manner, and delivering a diagnosis of a diseased condition of the tissue based on the measured impedance signals and reference values.

Hence, the present invention is based on the insight of the importance of measuring the impedance in, at least, the topmost layer of the skin with a sufficiently high spatial resolution, i.e. each measurement should only obtain impedance data from a small partition of the tissue under evaluation, in order to allow for a detection of small anomalies in the skin such as a diseased condition, e.g. malignant melanoma, squamos cell carcinoma, or basal cell carcinoma, at an early stage. By activating successive adjacent electrode pairs of the electrode, it is possible to achieve current paths that each run through a small partition of the tissue being in contact with the electrodes along the longitudinal direction of the electrodes, and that successively are moved through the topmost skin layer. Thereby, a scan with a high spatial resolution of the topmost layer of the skin can be achieved. Further, the present invention also enables to perform corresponding scans of tissue at deeper tissue layers. This can be achieved by successively activating or connecting electrode pairs having one or more intermediate electrodes in between. Accordingly, the present inventions provides for a two-dimensional scanning of tissue, i.e. in a depth dimension and a lateral dimension, with an improved spatial resolution in comparison with prior art.

According to an embodiment of the present invention, each electrode can be placed in one of at least three states including a first active state where the electrode is connected to the impedance measuring circuit to inject a measuring current into tissue of the subject, a second active state where the electrode is connected to the impedance measuring circuit to measure the resulting current from the tissue, and a floating state where the electrode is disconnected from the impedance measuring circuit. Further, each electrode may be placed in a fourth state where the electrode is connected to ground. By placing an electrode pair in the first and/or second state and the remaining electrodes in the third or fourth state, possible superficial current can be significantly reduced or eliminated. This is particularly useful if there are one or more intermediate electrodes between the active electrodes, i.e. the electrodes being involved in the measurement, since the measurement at deeper tissue layers will be more accurate due to the higher risk for superficial currents in such a measurement configuration.

According to another embodiment, the predetermined activation scheme includes activating two electrodes in the first state and in the second state and to place the remaining electrodes in the floating state in a successive manner to gradually scan a tissue of the subject at different tissue depths. Thereby, it is possible to efficiently scan different tissue depths and to obtain impedance data for a number of different adjacent partitions at different tissues depths. In other words, a tissue layer at a selected tissue depth can be gradually scanned and a tissue depth can be determined by selecting a number of intermediate electrodes between the activated pair of electrodes.

According to embodiments of the present invention, the applied current may have a frequency between 10 Hz and 10 MHz. For example, the measurements are performed using a number of frequencies in this frequency band at each electrode configuration. At higher frequencies (e.g. above about 100 kHz), the current paths will reach deeper down into the tissue for a given electrode configuration, i.e. spacing between the electrodes being used in the measurement, in comparison with lower frequencies (e.g. below about 500 Hz).

According to an embodiment, the probe is provided with electrodes that have an elongated rectangular shape and are arranged at the probe in parallel rows. However, there are a number of alternative designs. For example, the electrodes may be arranged as concentric rings, or as squares. The electrodes may be arranged with micro-needles wherein each electrode comprises at least one spike. The spikes are laterally spaced apart from each other and having a length being sufficient to penetrate at least into the stratum corneum. In an alternative embodiment, the electrodes are non-invasive and each electrode has a substantially flat surface adapted to be placed against the tissue of the subject. It is also possible to combine electrodes provided with micro-needles with non-invasive electrodes.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

BRIEF DESCRIPTION OF THE DRAWINGS

Exemplifying embodiments of the invention will be described below with reference to the accompanying drawings, in which.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. Even though particular types of probes including micro-invasive as well as non-invasive will be described, the invention is also applicable to other types of such as invasive probes.

Thus, preferred embodiments of the present invention will now be described for the purpose of exemplification with reference to the accompanying drawings, wherein like numerals indicate the same elements throughout the views. It should be understood that the present invention encompasses other exemplary embodiments that comprise combinations of features as described in the following. Additionally, other exemplary embodiments of the present invention are defined in the appended claims.

Figure 1:
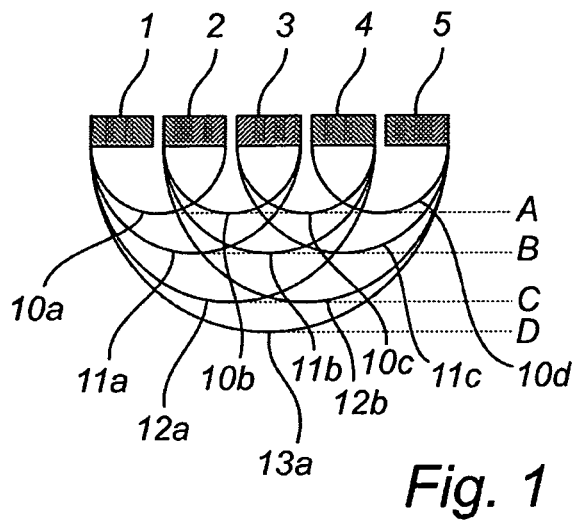
FIG. 1 is a schematic cross-sectional view of a probe according to an embodiment of the present invention.

Referring first to FIG. 1, a general description of the probe and the function of the probe will be given. In a preferred embodiment of the switch probe, a set of five rectangular electrode bars 1, 2, 3, 4, and 5 are arranged in the probe. The electrodes are adapted to be placed in direct contact with the skin. The embodiment illustrated in inter alia FIG. 1 including 5 electrodes, 5 electrodes where adjacent electrodes are separated with a distance of about 5 mm and having a length of about 5 mm, has shown to be a practical and useful configuration for detections of diseased conditions such as malignant melanoma, both with regard to spatial resolution in a lateral dimension and in a depth dimension. A skin area of about 25 mm$^2$ is thus covered by the probe and at high frequencies, above about 100 kHz, the deepest tissue layer being reached is about 2.5 mm which has been proven to be a clinical relevant depth. In order to cover a larger skin area, the probe can be moved to a neighbouring skin site. However, as the skilled person realizes, the probe may include more or less than five electrodes, for example 3 or 7 electrodes. Further, other electrode dimensions and other spacing between adjacent electrodes are conceivable, for example, electrodes having a width of about 4 mm and a length of about 8 mm.

In this preferred embodiment described in FIG. 1, the electrode bars are arranged to cover a skin area of 5×5 mm. The skin impedance is measured by applying an AC voltage over two of the electrodes and measuring the resulting current, which will be described in more detail below. By selecting adjacent pairs of electrodes, the topmost layer of the skin can be scanned in four steps, and by selecting pairs that are spaced further apart, i.e. electrode pairs with one or more intermediate electrodes, the resulting current path allows for measurement at deeper skin layers. This is illustrated in FIG. 1, where a number of currents paths are schematically indicated. By gradually activating pairs of adjacent electrodes, i.e. electrodes 1 and 2 or 2 and 3 and so on, four impedance measurements can be made in the topmost layer A of the skin by measuring the resulting current paths 10a, 10b, 10c, and 10d, and a scan of the topmost tissue layer can hence be achieved. Further, by gradually activating pairs of electrodes with one intermediate electrode in between, i.e. electrode 1 and 3, and 2 and 4 and so on, three impedance measurements can be made in a lower layer B of the skin by measuring the resulting current paths 11a, 11b, and 11c. Moreover, by gradually activating pairs of electrodes with two intermediate electrodes in between, i.e. electrode 1 and 4, and 2 and 5, two impedance measurements can be made in an even lower layer C of the skin by measuring the resulting current paths 12a, and 12b. Finally, a measurement can be made at a fourth depth D by activating the outer electrodes 1 and 5 and measuring the resulting current path 13a. Accordingly, it is possible to obtain a two-dimensional scan of the tissue, i.e. a scan in a depth dimension, illustrated by the e.g. currents paths 10a, 11a, 12a, and 13a, and a scan in the lateral dimension at each layer, illustrated e.g. by the currents paths 10a, 10b, 10c, and 10d.

In this exemplifying embodiment of the probe according to the present invention, there are ten possible ways of selecting electrode pairs. The possibility to measure inter alia the topmost skin layer in small (determined inter alia by the spacing between adjacent electrodes and the frequency of the applied current) consecutive partitions is important since it allows for detection of small anomalies in the skin and tissue.

Each electrode of the probe may be set in four different states:

Inject: The electrode is set to inject measurement current into the tissue. The respective electrode 1-5 is connected to $V_{exc}$ by closing the respective switch S1a-S1d (see FIG. 2);

Measure: The resulting current from the tissue is measured via the electrode. The respective electrode 1-5 is connected to $I_{meas}$ by closing the respective switch S2a-S2d (see FIG. 2);

Ground: The electrode is grounded to prevent leakage of superficial current when measurements are performed using other electrodes. The respective electrode 1-5 is connected to GND by closing the respective switch S3a-S3e; and Floating: The electrode is disconnected. The respective electrode 1-5 is disconnected from $V_{exc}$, $I_{meas}$, and GND by opening all respective switches S1a-S1d, S2a-S2d, and S3a-S3E.

Figure 2:
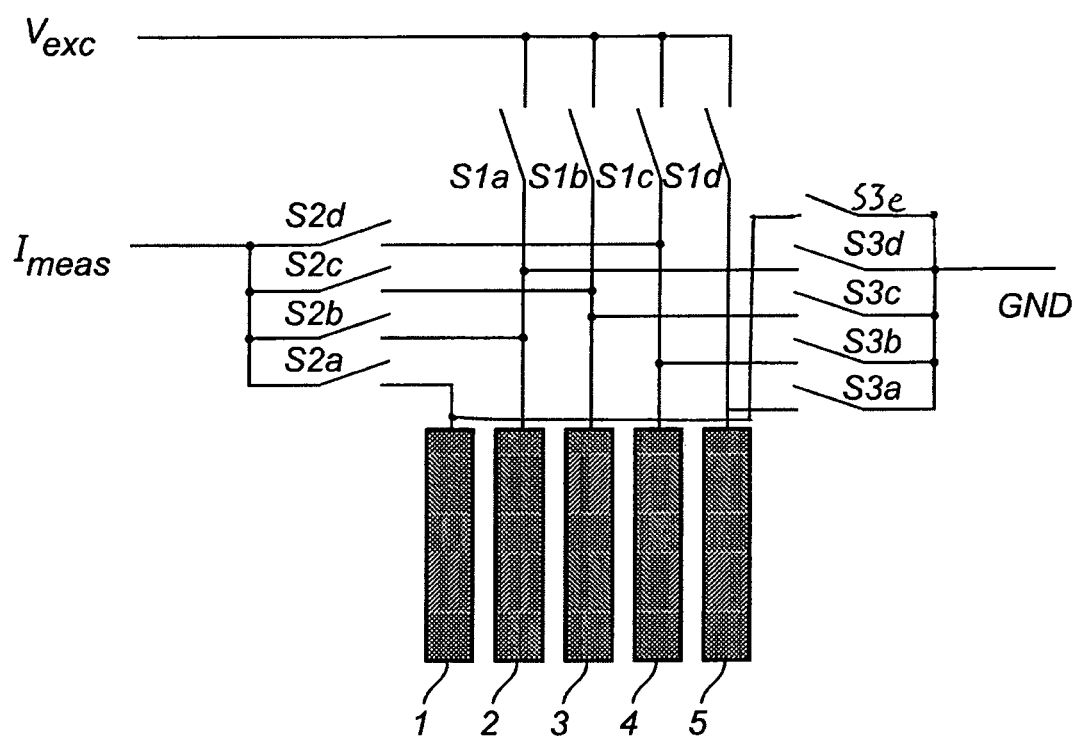
FIG. 2 is a schematic illustration of the switched electrode according to an embodiment of the present invention.

Turning now to FIG. 2, the principles of the switched electrode will be discussed. The embodiment shown in FIG. 2 includes five electrodes and thirteen switches but, as the skilled man realizes, this is only an example. For example, the probe according to the invention may include six, seven, or nine electrodes (which are non-exhaustive examples), which, of course, will require a larger number of switches. With reference to FIG. 2, during a measurement, only one S1 switch and S2 switch, respectively, is closed. For example, by closing switches S1b and S2b, a measurement between electrode bars 2 and 3 is possible since electrode 2 and 3 are connected to $V_{exc}$ and $I_{meas}$, respectively. This measurement configuration will provide impedance data for the topmost tissue layer. With reference to FIG. 1, using this measurement configuration the resulting current path will be 10b. If, on the other hand, the switches S1d and S2a are closed, a measurement between electrodes 1 and 5 is enabled since electrodes 5 and 1 are connected to $V_{exc}$ and $I_{meas}$, respectively. This measurement configuration will provide impedance data from a relatively deep layer of the tissue about 2.5 mm, with reference to FIG. 1, the resulting current path will be 13a. To eliminate potential superficial currents the remaining electrodes 2, 3, and 4 can be connected to ground GND by closing switches S3d, S3c, and S3b. The measurement configuration with electrodes 1 and 5 activated for measurement enables gathering of impedance data from the deepest tissue layer that is possible to reach using the embodiment described with reference to FIGS. 1 and 2. If there is an interest in reaching even deeper down in the tissue an embodiment with, for example, seven electrodes can be used or an embodiment with increased distance or spacing between respective electrodes. As discussed above, using higher frequencies, e.g. above 100 kHz, also entails measurements at a lower tissue layer in the depth dimension. In preferred embodiments analog switch integrated circuits with low on-state resistance are used, but there are other possible alternatives, for example, electromechanical relays or mechanical relays.

Figure 3:
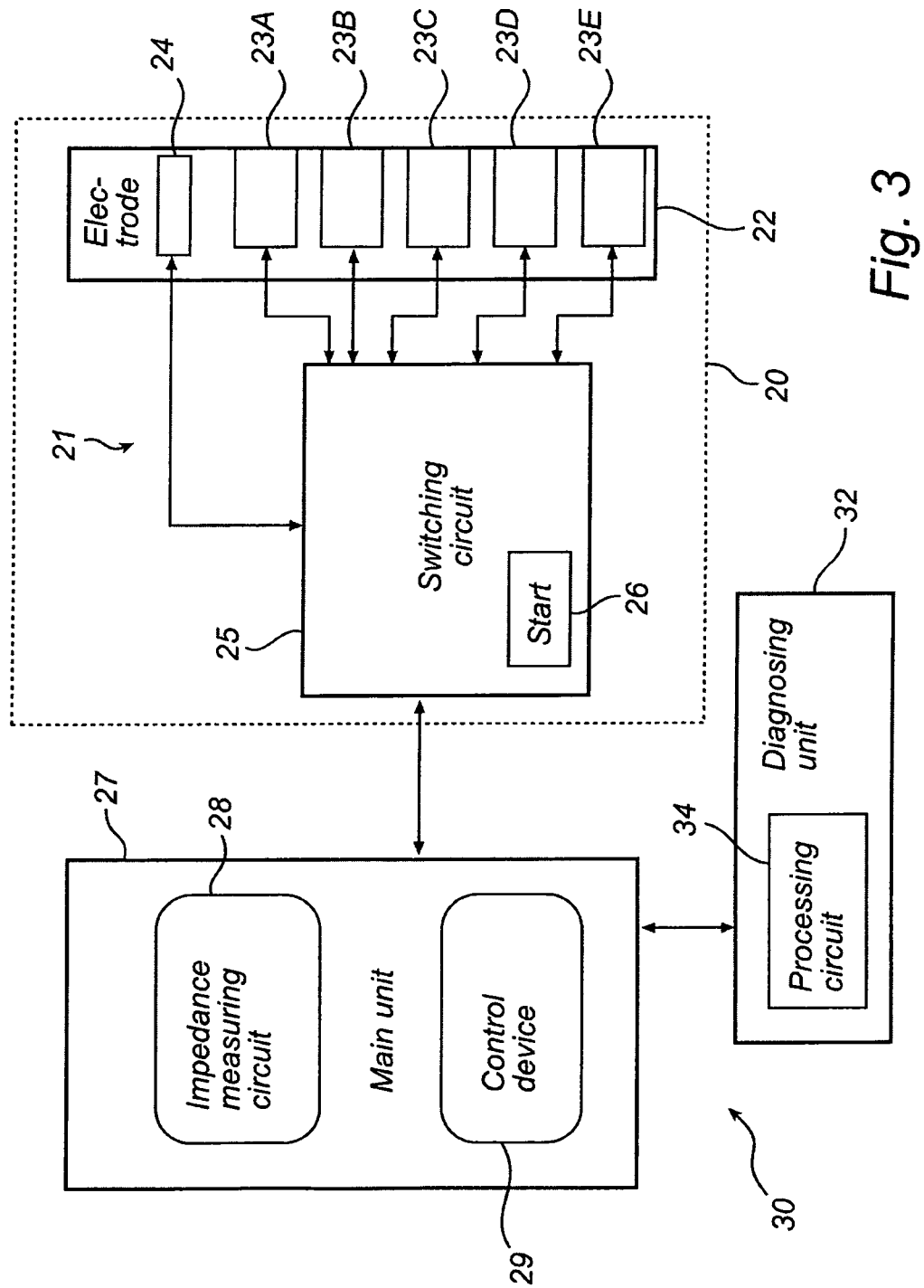
FIG. 3 is schematic illustration of an embodiment of a measurement device including a probe in accordance with FIGS. 1 and 2.

With reference to FIG. 3, an embodiment of a measurement device according to the present invention for measuring electrical impedance of tissue of a subject using the probe including electrodes and a switching unit as described with reference to FIGS. 1 and 2 will be discussed. The measurement device 20 includes a probe 21, e.g. a probe as discussed above with reference to FIGS. 1 and 2. The probe 21 comprises an electrode part 22 provided with five electrode bars 23A-23B and an identification chip 24, which may be used for re-control of the disposable electrode part 22. A switching circuit 25 is releasably connected to the electrode part 22 via an interface (not shown). Further, the switching circuit 25 includes an activation button 26 allowing a user to initiate a measurement procedure on a patient to obtain impedance data from different tissue depths according to a predetermined activation procedure. The probe 21 may be connected to a main unit 27 including an impedance measuring circuit 28 adapted to apply a voltage at two of the electrodes 23A-23E and to measure a resulting current via the electrodes 23A-23E to determine an impedance signal. The impedance measuring circuit 28 is adapted to apply a current having at least two frequencies between about 10 Hz and about 10 MHz. Moreover, the main unit 27 also includes a control device 29 adapted to control the switching circuit 25 to activate electrodes 23A-23E in accordance with the predetermined activation procedure or scheme. The predetermined activation scheme includes inter alia an activation of adjacent electrodes in a successive manner to gradually scan tissue of the subject at a first tissue depth, which scanned tissue depth depends to a large extent on spacing between the activated electrode pair, so as to obtain a matrix of impedance signals from the tissue depth. In a system environment 30, the main unit may be connected to a diagnosing unit 32. In an alternative embodiment, the diagnosing unit 32 may be integrated in the main unit 27. The main unit 27 and the diagnosing unit 32 may include storage units (not shown) for storing, for example, obtained impedance data and reference data, for example, from a reference measurement performed on the same patient. The main unit 27 or the diagnosing unit 32 may also include a processing circuit 34, in this embodiment included in the diagnosing unit 32, adapted to process obtained impedance data to reduce the number of variables by removing insignificant variables by performing linear or non-linear projections of the impedance data to lower subspaces. In preferred embodiments of the present invention, principal component analysis (PCA) is used. An alternative approach is to use parallel factor analysis (PARAFAC). Further, classification rules determined by means of, for example, linear discriminant analysis (LDA) or soft independent modelling of class analogy (SIMCA) may be used to improve the diagnosing. This is described in more detail in a co-pending patent application "Method for diagnosis of skin cancer" by the same applicant. Further, see also, for example, "Skin cancer as seen by electrical impedance", P. Åberg, Department of Laboratory Medicine, Karolinska Institutet, Stockholm, Sweden, 2004.

Moreover, the diagnosing unit 32 and/or the main unit 27 may include display means for displaying a diagnosis result from the diagnosis. The diagnosing unit 32 compares the obtained and processed impedance spectrum, including impedance data obtained at different tissue depths and at different locations in relation to the probe as have been described above in reference with FIGS. 1 and 2 and at different frequencies, with reference data to obtain a diagnosis of a diseased condition of the skin, for example, basal cell carcinoma, squamous cell carcinoma, or malignant melanoma.

The measurements are performed at the (suspected) diseased skin site and at a reference site with normal (unaffected) skin, for example, in accordance with the approach described in Emtestam I, Nicander, I, Stenström M, Ollmar, S., "Electrical impedance of nodular basal cell carcinoma: a pilot study", Dermatology 1998; 197: 313-316, and Kapoor S. "Bioelectric impedance techniques for clinical detection of skin cancer using simple electrical impedance indices", Skin Res Technol 2003; 9: 257-261, and Beetner D G, Kapoor S, Manjunath S, Zhou X, Stoecker W V "Differentation among basal cell carcinoma, benign lesions, and normal skin using electric impedance", IEEE Trans Biomed Eng 2003; 50: 1020-1025. However, it should be noted that the measurements described in these references were obtained using a conventional probe and an early version of the impedance spectrometer.

According to an embodiment of the present invention, each electrode is provided with micro-needles, thereby forming a micro-needled surface. As has been discussed above, the probe, in a preferred embodiment, includes five rectangular areas or bars. In this configuration, each bar contains an array of, for example, 57 (19×3) micro-needles. Each bar is about 1 mm wide and 5 mm long. The distance between adjacent bars is about 0.2-0.5 mm. The active part of the probe is thus about 5×5 mm. Each micro-needle has a length of approximately 100 micrometer, as measured from its base, and a thickness of at least 20 micrometer. The electrode bars and micro-needles can be made of plastic material in a moulding process. The material could be made intrinsically conductive or covered with a conductive layer such as gold. In an alternative embodiment, the electrode bars and micro-needles are made of silicon and covered with gold having a thickness of at least 2 micrometer. However, other materials comprising a conductive surface with similar dimensions would work, but it should be selected to be biocompatible. In, for example, the patent applications EP 1959828, EP 1600104, and EP 1437091 by the same applicant, different probe concepts having such micro-needles are described.

In another embodiment, the electrode bars are non-invasive and substantially flat. In, for example, U.S. Pat. No. 5,353,802 by the same applicant, a probe concept including non-invasive electrodes has been described.

Although exemplary embodiments of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

The invention claimed is:

1. A probe for measuring electrical impedance of tissue of a subject comprising a plurality of electrodes, said probe being adapted to be placed in direct contact with the skin of the subject, said probe further comprising:
    a switching circuit for selectively connecting each electrode with an impedance measuring circuit, wherein said impedance measuring circuit is adapted to apply a voltage between two active electrodes and measure a resulting current flowing between said two active electrodes, or to inject a current flowing between said two active electrodes and measure a resulting voltage between said two active electrodes, to determine an impedance signal; and wherein
    said switching circuit is adapted to connect each electrode such that said electrode functions in one of at least three states including:
        a first active state where said electrode is connected to the impedance measuring circuit to inject said current into or to apply said voltage to the tissue of said subject,
        a second active state where said electrode is connected to said impedance measuring circuit to measure the resulting current or the resulting voltage from the tissue, and
        an inactive state where said electrode is disconnected from said impedance measuring circuit; and wherein
    said switching circuit is adapted to receive control signals instructing said switching circuit to activate electrode pairs, one active electrode in said first active state and the other active electrode in said second active state to form the two active electrodes connected to the impedance measuring circuit, and to deactivate remaining electrodes by switching the remaining electrodes to the inactive state, in accordance with a predetermined activation scheme, said predetermined activation scheme including to activate said electrode pairs and deactivate said remaining electrodes in a successive manner to gradually scan tissue of said subject at least at a first tissue depth so as to obtain a sequence of impedance signals from said at least first tissue depth, wherein said electrode pairs are made of adjacent electrodes.

2. The probe according to claim 1, wherein said predetermined activation scheme further includes successively activating additional pairs of electrodes, each additional pair having one electrode in said first active state and the other in said second active state, wherein said additional pairs of electrodes have at least one intermediate electrode arranged in between, to gradually scan the tissue of said subject at different tissue depths, wherein said different tissue depths are determined by selecting the number of intermediate electrodes.

3. The probe according to claim 1, wherein said electrodes have an elongated rectangular shape and are arranged on said probe in parallel rows.

4. The probe according to claim 1, wherein said inactive state comprises a third floating state wherein said electrode is disconnected and a fourth state wherein said electrode is connected to ground.

5. The probe according to claim 4, wherein said switching circuit is adapted to deactivate said remaining electrodes by placing at least one remaining electrode in said third floating state or to connect said at least one remaining electrode to ground in said fourth state.

6. A measurement device for measuring electrical impedance of tissue of a subject comprising a probe having a plurality of electrodes, said electrodes being adapted to be placed in direct contact with the skin of the subject, said measurement device further comprising:
    an impedance measuring circuit;
    a switching circuit for selectively connecting each electrode with said impedance measuring circuit, wherein said impedance measuring circuit is adapted to apply a voltage between two active electrodes and measure a resulting current flowing between said two active electrodes, or to inject a current flowing between said two active electrodes and measure a resulting voltage between said two active electrodes, to determine an impedance signal; and wherein
    said switching circuit is adapted to connect each electrode such that said electrode functions in one of at least three states including:
        a first active state where said electrode is connected to the impedance measuring circuit to inject said current into or to apply said voltage to the tissue of said subject,
        a second active state where said electrode is connected to said impedance measuring circuit to measure the resulting current or the resulting voltage from the tissue, and
        an inactive state where said electrode is disconnected from said impedance measuring circuit; and
    a control device adapted to control said switching circuit to activate electrode pairs, one active electrode in said first active state and the other active electrode in said second active state to form the two active electrodes connected to the impedance measuring circuit, and to deactivate remaining electrodes by switching the remaining electrodes to the inactive state, in accordance with a predetermined activation scheme, said predetermined activation scheme including to activate said electrode pairs and deactivate said remaining electrodes in a successive manner to gradually scan tissue of said subject at least at a first tissue depth so as to obtain a sequence of impedance signals from said at least first tissue depth, wherein said electrode pairs are made of adjacent electrodes.

7. The measurement device according to claim 6, wherein said predetermined activation scheme further includes successively activating additional pairs of electrodes, each additional pair having one electrode in said first active state and the other in said second active state, wherein said additional pairs of electrodes have at least one intermediate electrode arranged in between, to gradually scan the tissue of said subject at different tissue depths, wherein said different tissue depths are determined by selecting the number of intermediate electrodes.

8. The measurement device according to claim 6, wherein said inactive state comprises a third floating state wherein said electrode is disconnected and a fourth state wherein said electrode is connected to ground.

9. The measurement device according to claim 8, wherein said switching circuit is adapted to deactivate said remaining electrodes by placing at least one remaining electrode in said third floating state or to connect said at least one remaining electrode to ground in said fourth state.

10. A medical system for diagnosing a diseased condition of the skin of a subject comprising a probe for measuring electrical impedance of tissue of a subject, said probe being provided with a plurality of electrodes adapted to be placed in direct contact with the skin of the subject, comprising:
    an impedance measuring circuit;
    a switching circuit for selectively connecting each electrode with said impedance measuring circuit, wherein said impedance measuring circuit is adapted to apply a voltage between two active electrodes and measure a resulting current flowing between said two active electrodes, or to inject a current flowing between said two active electrodes and measure a resulting voltage between said two active electrodes, to determine an impedance signal; and wherein
    said switching circuit is adapted to connect each electrode such that said electrode functions in one of at least three states including:
        a first active state where said electrode is connected to the impedance measuring circuit to inject said current into or to apply said voltage to the tissue of said subject,
        a second active state where said electrode is connected to said impedance measuring circuit to measure the resulting current or the resulting voltage from the tissue, and
        an inactive state where said electrode is disconnected from said impedance measuring circuit;
    a control device adapted to control said switching circuit to activate electrode pairs, one active electrode in said first active state and the other active electrode in said second active state to form the two active electrodes connected to the impedance measuring circuit, and to deactivate remaining electrodes by switching the remaining electrodes to the inactive state, in accordance with a predetermined activation scheme, said predetermined activation scheme including to activate said electrode pairs and deactivate said remaining electrodes in a successive manner to gradually scan tissue of said subject at least at a first tissue depth so as to obtain a sequence of impedance signals from said at least first tissue depth, wherein said electrode pairs are made of adjacent electrodes; and
    a diagnosing unit being adapted to obtain said sequence of impedance signals and to deliver a diagnosis of a diseased condition of the tissue based on the sequence of impedance signals and reference values.

11. A medical system for diagnosing a diseased condition of the skin of a subject comprising a probe for measuring electrical impedance of tissue of a subject, said probe being provided with a plurality of electrodes adapted to be placed in direct contact with the skin of the subject, comprising:
    an impedance measuring circuit;
    a switching circuit for selectively connecting each electrode with said impedance measuring circuit, wherein said impedance measuring circuit is adapted to apply a voltage between two active electrodes and measure a resulting current flowing between said two active electrodes, or to inject a current flowing between said two active electrodes and measure a resulting voltage between said two active electrodes, to determine an impedance signal; and wherein
    said switching circuit is adapted to connect each electrode such that said electrode functions in one of at least three states including:
        a first active state where said electrode is connected to the impedance measuring circuit to inject said current into or to apply said voltage to the tissue of said subject,
        a second active state where said electrode is connected to said impedance measuring circuit to measure the resulting current or the resulting voltage from the tissue, and
        an inactive state where said electrode is disconnected from said impedance measuring circuit, said inactive state comprising a third floating state wherein said electrode is disconnected and a fourth state wherein said electrode is connected to ground,
    a control device adapted to control said switching circuit to activate electrode pairs, one active electrode in said first active state and the other active electrode in said second active state to form the two active electrodes connected to the impedance measuring circuit, and to deactivate remaining electrodes by switching the remaining electrodes to the inactive state, in accordance with a predetermined activation scheme, said predetermined activation scheme including to activate said electrode pairs and deactivate said remaining electrodes in a successive manner to gradually scan tissue of said subject at a selected tissue depth so as to obtain a sequence of impedance signals from said selected tissue depth,
        wherein said electrode pairs are made of adjacent electrodes or two electrodes having at least one intermediate electrode arranged in between, wherein said selected tissue depth is determined by selecting a number of intermediate electrodes; and
    a diagnosing unit being adapted to obtain said sequence of impedance signals and to deliver a diagnosis of a diseased condition of the tissue based on the sequence of impedance signals and reference values.

12. A method for diagnosing a diseased condition of the skin of a subject utilizing a probe for measuring electrical impedance of tissue of the subject, said probe being provided with a plurality of electrodes adapted to be placed in direct contact with the skin of the subject, and wherein each electrode is adapted to function in one of at least three states including: a first active state where said electrode is connected to an impedance measuring circuit to inject a current into or to apply a voltage to said tissue; a second active state where said electrode is connected to said impedance measuring circuit to measure a resulting current or a resulting voltage from the tissue; and an inactive state where said electrode is disconnected from said impedance measuring circuit; said method comprising:

placing the electrodes on the skin of the subject;

selectively activating electrode pairs with one active electrode in said first active state and the other active electrode in said second active state to form two active electrodes connected to the impedance measuring circuit and deactivating remaining electrodes by switching the remaining electrodes to the inactive state, in accordance with a predetermined activation scheme;

using said impedance measuring circuit to apply a voltage between said two active electrodes and measure said resulting current flowing between said two active electrodes, or to inject a current to flow between said two active electrodes and measure a resulting voltage between said two active electrodes, to determine an impedance signal;

gradually scanning said tissue of said subject at least at a first tissue depth so as to obtain a sequence of impedance signals from said at least first tissue depth by controlling activation of electrodes in accordance with said predetermined activation scheme, said predetermined activation scheme including activating adjacent electrodes in a successive manner; and delivering a diagnosis of a diseased condition of the tissue based on the sequence of impedance signals and reference values.

13. The method according to claim 12, wherein said predetermined activation scheme further includes successively activating additional pairs of electrodes, each additional pair having one electrode in said first active state and the other in said second active state, wherein said additional pairs of electrodes have at least one intermediate electrode arranged in between, to gradually scan the tissue of said subject at different tissue depths, wherein said different tissue depths are determined by selecting the number of intermediate electrodes.

14. The method according to claim 12, wherein said inactive state comprises a third floating state wherein said electrode is disconnected and a fourth state wherein said electrode is connected to ground.

15. The method according to claim 12, wherein said deactivating said remaining electrodes is performed by placing at least one remaining electrode in said third floating state or to connect said at least one remaining electrode to ground in said fourth state.

* * * * *